United States Patent
Huang et al.

(10) Patent No.: US 11,896,525 B2
(45) Date of Patent: Feb. 13, 2024

(54) LASER THERMAL CONJUNCTIVOPLASTY

(71) Applicant: Oregon Health & Science University, Portland, OR (US)

(72) Inventors: David Huang, Portland, OR (US); Gangjun Liu, Portland, OR (US); Jianlong Yang, Portland, OR (US); Stephen Pflugfelder, Houston, TX (US)

(73) Assignees: OREGON HEALTH & SCIENCE UNIVERSITY, Portland, OR (US); BAYLOR COLLEGE OF MEDICINE, Houston, TX (US)

( * ) Notice: Subject to any disclaimer, the term of this patent is extended or adjusted under 35 U.S.C. 154(b) by 156 days.

(21) Appl. No.: 16/487,629

(22) PCT Filed: Feb. 27, 2018

(86) PCT No.: PCT/US2018/019886
§ 371 (c)(1),
(2) Date: Aug. 21, 2019

(87) PCT Pub. No.: WO2018/157110
PCT Pub. Date: Aug. 30, 2018

(65) Prior Publication Data
US 2020/0030141 A1    Jan. 30, 2020

Related U.S. Application Data

(60) Provisional application No. 62/464,288, filed on Feb. 27, 2017.

(51) Int. Cl.
*A61F 9/008*    (2006.01)
*A61B 17/285*    (2006.01)
(Continued)

(52) U.S. Cl.
CPC .......... *A61F 9/008* (2013.01); *A61B 17/285* (2013.01); *A61B 18/203* (2013.01); *A61B 18/22* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 5,217,460 A | 6/1993 | Knoepfler | |
| 2002/0111608 A1* | 8/2002 | Baerveldt | A61F 9/00745 606/6 |

(Continued)

FOREIGN PATENT DOCUMENTS

| | | |
|---|---|---|
| EP | 2705805 | 3/2014 |
| WO | 2012158788 | 11/2012 |
| WO | 2016196196 | 12/2016 |

OTHER PUBLICATIONS

Arenas et al. "A New Surgical Approach for the Treatment of Conjunctivochalasis: Reduction of the Conjuctival Fold with Bipolar Electrocautery Forceps", The Scientific World Journal, vol. 2016 (2016), Article ID 6589751. 4 pages, downloaded Aug. 20, 2019 <http://https://www.ncbi.nlm.nih.gov/pmc/articles/PMC4856897>.

*Primary Examiner* — Scott Luan
(74) *Attorney, Agent, or Firm* — Schwabe, Williamson & Wyatt, P.C.

(57) ABSTRACT

Disclosed is a handheld laser probe for laser thermal conjunctivoplasty, the handheld laser comprising: a forceps; and a line focused laser light source coupled to the forceps, wherein the forceps are configured to grasp a conjunctival fold and hold the fold in a light beam of the line focused laser, and wherein the line focused laser beam is configured to uniformly heat the conjunctival fold held in the forceps. Disclosed are systems for laser thermal conjunctivoplasty (Continued)

including the handheld laser. Disclosed are methods of conjunctivoplasty using the handheld laser probe.

15 Claims, 21 Drawing Sheets

(51) Int. Cl.
    *A61B 18/20*          (2006.01)
    *A61B 18/22*          (2006.01)
    *A61B 17/00*          (2006.01)

(52) U.S. Cl.
    CPC ............... *A61B 2017/00973* (2013.01); *A61F 2009/00853* (2013.01); *A61F 2009/00865* (2013.01)

(56) References Cited

U.S. PATENT DOCUMENTS

| | | | |
|---|---|---|---|
| 2013/0253489 A1* | 9/2013 | Nau, Jr. | A61B 17/29 606/16 |
| 2014/0066911 A1* | 3/2014 | Nau, Jr. | A61B 18/20 606/8 |
| 2014/0121508 A1 | 5/2014 | Latimer et al. | |
| 2017/0231689 A1* | 8/2017 | Igarashi | A61B 18/22 600/479 |

* cited by examiner

LASER THERMAL CONJUNCTIVOPLASTY

CROSS-REFERENCE

This application claims priority benefit of the earlier filing date of U.S. Provisional Application No. 62/464,288, filed Feb. 27, 2017, which is incorporated herein by reference in its entirety.

STATEMENT OF GOVERNMENT INTEREST

This invention was made with government support under 5 UL1 TR000128 10 awarded by the NIH National Center for Advancing Translational Sciences.

TECHNICAL FIELD

Embodiments herein relate to the field of eye surgery, and, more specifically, to a device for, and methods of, performing laser eye surgery.

BACKGROUND

The white part of the eye (sclera) is covered by a clear membrane called the conjunctiva. Like skin, the conjunctiva becomes loose and wrinkly with age. This degenerative condition is called conjunctivochalasis. The loose folds of conjunctiva often disrupt the uniform distribution of tears and can cause constant eye irritation and blurred vision. In severe cases, the conjunctival folds protrude onto the inferior eye lid margin and are traumatized by the lid during blinking. Furthermore, the lid skin is also irritated and altered by the displaced tear.

Conjunctivochalasis is a common cause of tear dysfunction (also referred to as "dry eye"); however, it does not respond to the usual dry eye treatments such as artificial tears, punctal plugs and anti-inflammatory drops. Effective treatment requires surgical reduction or excision of the redundant conjunctival tissue to reestablish the inferior tear meniscus and normal tear dynamics. Conjunctivochalasis is typically diagnosed by evaluating the conjunctiva for redundant folds that prolapse onto the lower eyelid and obliterate the tear meniscus in that region (see FIGS. 1A to 1C). Cross-sectional optical coherence tomography (OCT) is typically used to evaluate the severity of the condition and the effectiveness of surgery to remove the redundant tissue.

Surgical means used to remove redundant conjunctival tissue is an effective way to treat conjunctivochalasis. However, the current surgical techniques, such as thermocautery or electrocautery, are not performed on a widespread basis due to the long painful healing period. Thermocautery is performed with a battery powered hot wire; while electrocautery is performed using a radiofrequency diathermy probe. Both techniques reach very high temperatures exceeding the point of water boiling and burn the conjunctival epithelium and underlying stroma. Additionally, the burn often extends to the surrounding tissue. This creates a full thickness burn wound that is generally painful, takes up to one month to fully heal and occasionally induces excessive inflammation and scarring. Furthermore, a chronic inflammatory conjunctival mass called pyogenic granuloma could result, which would necessitate long-term anti-inflammatory eye drops and possibly further surgery. Poor cosmetic appearance (red blots due to bleeding in surface tissue) during the long healing period also deters patients. Surgical conjunctival excision with the addition of an amniotic membrane transplant (attached by fibrin glue or suture) can improve the healing course, but must be performed in the operating room, which markedly increases cost. Thus, the need exist for new and improved surgical techniques to treat conjunctivochalasis and other disorders.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1A:
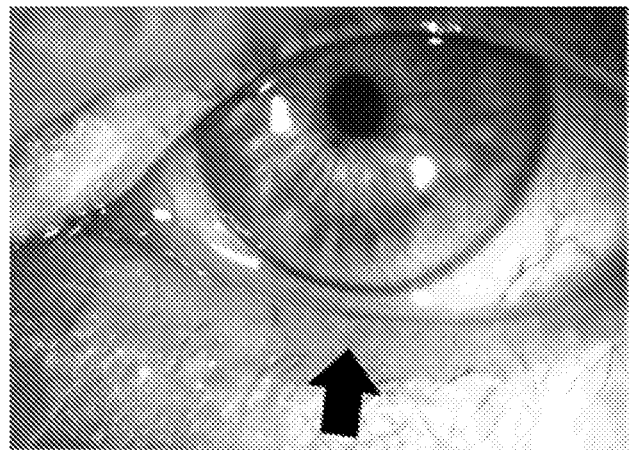
FIGS. 1A-1C are digital images showing: (A) a photograph of conjunctivochalasis, with the an arrow pointing to redundant conjunctiva; (B) an image of fluorescein stained conjunctivochalasis, with an arrow showing lid parallel folds; and (C) an optical coherence tomography image of conjunctivochalasis, with an arrow showing obliteration of the tear meniscus.
Figure 1B:
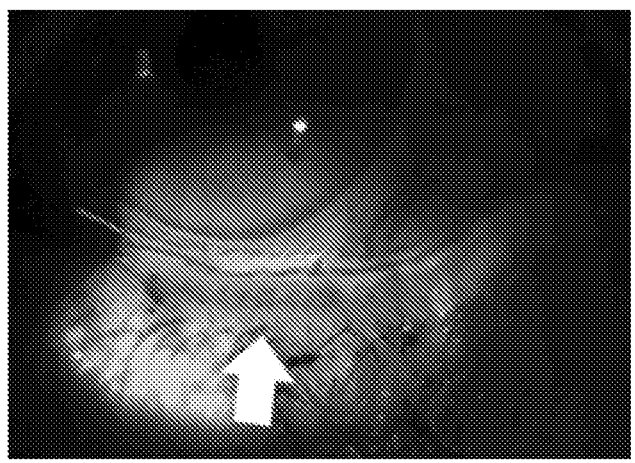
Figure 1C:
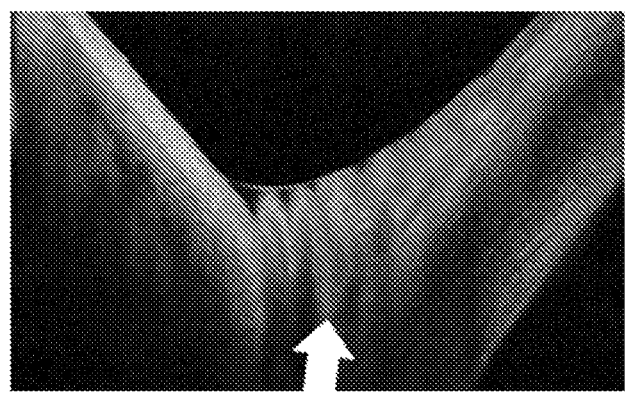

In the following detailed description, reference is made to the accompanying drawings, which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for the sake of clarity.

Disclosed herein are a laser thermal conjunctivoplasty (LTC) device, system, and method that provides a safe, fast procedure to treat conjunctivochalasis, for example, in an ophthalmologist's office, by heating and shrinking large volumes of conjunctiva with minimized collateral damage and scarring.

Aspects of the present disclosure relate to a handheld laser probe for laser thermal conjunctivoplasty. In embodiments, the handheld laser probe includes forceps, such as angled forceps, and a line focused laser light source, such as a pulsed laser source coupled to the forceps, for example, mechanically coupled. By line focused laser light, it is meant that a lens or other device focuses the light to form a line. In other words, the light in the focal plane would have the appearance of a line. In embodiments, the forceps are configured to grasp a conjunctival fold and hold the fold in the light beam of the line focused laser while the line focused laser beam is configured to uniformly heat the fold, thereby shrinking large volumes of conjunctiva. In embodiments, the handheld laser probe device is designed to heat the conjunctival stroma as uniformly as possible to a temperature high enough for collagen shrinkage, but not so high as to cause boiling, mechanical disruption, blood vessel rupture, or bleeding. In embodiments, the laser beam focuses to a 10 mm line parallel to and just above the angled platform of the forceps (See e.g. FIG. 4C). In embodiments, the handheld laser probe includes a cylindrical lens to focus the laser light into a line. In embodiments, the handheld laser probe includes a pair of angled forceps, for example angled forceps can be used to grasp a conjunctival fold while the line focused laser beam is configured to uniformly heat the fold, thereby shrinking large volumes of conjunctiva. In some embodiments, the angled forceps have tips, forming grasping platforms that are angled about 30° to about 90° relative to the long axis of the body of the forceps, for example about, 30° to about 60° or even about 45° relative to the long axis of the body of the forceps. In some embodiments, the grasping platforms have a length that is about the same length as the line focused laserbeam, for example having a length of about 5 to about 15 mm, such as about 10 mm, such as measured from the bend to the tip of the grasping platform. In embodiments, the handheld laser probe includes a line focused laser light source selected with a laser wavelength, power, pulse duration, and beam focus width to heat water in conjunctival tissue to shrink its full thickness. In embodiments, the handheld laser probe includes a line focused laser beam that has a focal plane with length of about 10 mm and a width of about 1 mm.

Because nearly 80% of conjunctiva tissue is water, in embodiments, a laser wavelength is selected at which water is the dominant absorber in tissue. In addition, in embodiments, a laser wavelength is selected so the absorption length is matched to the thickness of conjunctival tissue. The thickness of the human conjunctiva is approximately 0.24 mm, and loose conjunctiva folded over when grasped by the surgical forceps should be approximately 0.5 mm thick. Thus, in embodiments, a wavelength is selected to heat conjunctival tissue to approximately 0.5 mm depth, i.e. the approximate thickness of the conjunctiva folded over. In addition, the energy, power, duration, and/or duty cycle of the laser pulse is chosen so that conjunctival tissue temperature is raised to the point of collagen shrinkage but not high enough to cause cellular or vascular rupture. This is much gentler and more controlled than standard surgical electrocautery, which is heated to the point of tissue vaporization when used to cut conjunctiva. Thus, the disclosed device, system and method provide for a drastic improvement over the techniques currently used in the art.

Generally, infrared light absorption in water is higher for longer wavelengths. The desirable absorption wavelengths for water can be found in the near infrared wavelength band, for example a wavelength from about 1.3 µm to about 2.4 µm. Thus, in embodiments a laser light source is selected that has a wavelength has a water absorption coefficient of 0.1 cm$^{-1}$ to 100 cm$^{-1}$, for example, from about 1.3 µm to about 2.4 µm, such as any value in between about 1.3 µm and about 2.4 µm.

Figure 2:
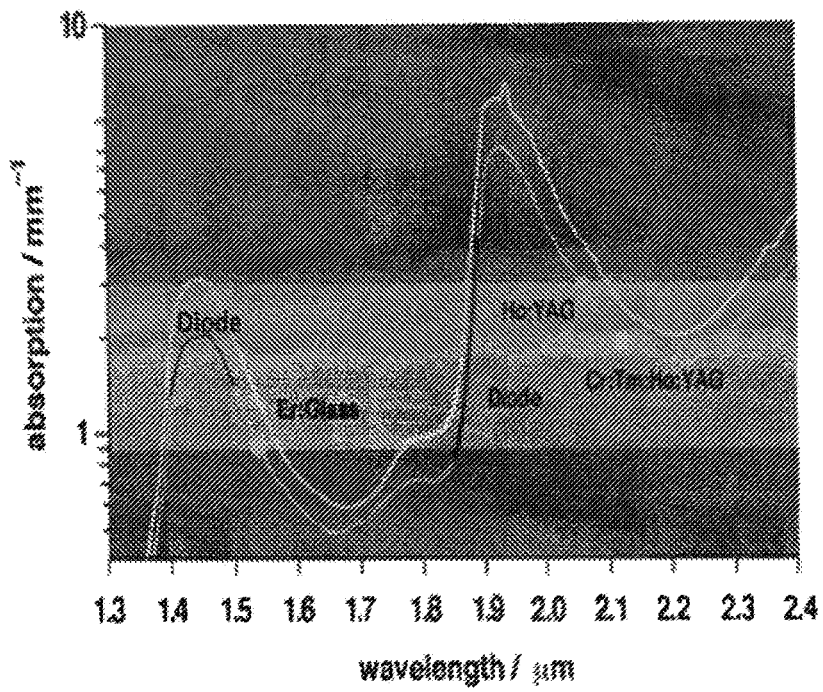
FIG. 2 is a graph of the absorption coefficient of infrared light for water and tissue (assuming 80% water content). A desirable absorption coefficient of 0.9 to 3 $mm^{-1}$ (light band) is available using diode lasers or solid state lasers.

From the water absorption spectrum (see FIG. 2), it can be seen that there are two wavelength bands in tissue that correspond to the wavelength available from commercially available diode lasers. Diode lasers are preferable to other laser sources because of their compactness, low cost, and reliability. For example, from FIG. 2, it can be determined that there is one good diode laser choice at 1.45 µm, and another at 1.9 µm. The 1.45 µm laser diode has higher performance and lower cost due to its wide use for telecommunications. Thus, in embodiments, a diode laser with a wavelength of about 1.45 µm is used for the disclosed device, system, and method. It should be noted, however, that other lasers, such as the 1.9 µm diode laser, a Ho:YAG laser, and a Cr:Tm:Ho:YAG laser are suitable for use in the disclosed devices, systems, and method. Furthermore, while the lasers discussed above may be optimal for the disclosed devices, systems, and methods, other lasers could be used as well.

As disclosed, the handheld laser probe includes a pair of forceps to grasp a conjunctival fold and a line focused laser beam to uniformly heat the fold. The laser energy is typically applied in pulses that confine the peak heating to the conjunctival fold. In embodiments, the laser light source of the handheld laser probe is a pulse laser. Since the conjunctiva is approximately 0.24 mm thick as a single layer, the fold held by the forceps would be approximately 0.5 mm. By using a beam focused into a line with a length of between about 5 mm and about 15 mm, such as about 10 mm, and a width of between about 0.5 mm and about 2 mm, such as about 1 mm, the laser can be focused specifically on the conjunctival fold, thereby reducing the chances of non-selective heating. By holding or grasping the conjunctival fold with an angled platform of angled forceps, the line focused laser beam heats the tissue along the angled platform of the forceps. In addition, the forceps may be used to lift the conjunctival fold off the sclera and thereby minimize the chance of damaging the underlying sclera, ciliary body, choroid, and retina. In embodiments, multiple pulses of laser light are delivered to achieve collagen shrinkage, which can be directly visualized by the surgeon. The number of pulses that are delivered to the tissue may be controlled by a foot pedal.

Aspects of the present disclosure are drawn to a system for laser thermal conjunctivoplasty. In embodiments, the system includes a handheld laser probe configured for laser thermal conjunctivoplasty, such as described herein, a laser coupled to the handheld laser probe; and a control system coupled to the laser. In some embodiments, the handheld laser probe is coupled to the laser by a multimode optical fiber. In embodiments, the control system includes a foot pedal. In embodiments, the control system includes a controlling circuit to control the laser pulse frequency, duty cycle and pulse energy. In embodiments, the control system includes a modulator for converting continuous-wave (CW) laser light from the portable laser coupled into pulses. In embodiments, the control system includes an optical switch/shutter 140 so that the optical switch/shutter, which can be coupled to and/or actuated by a foot pedal, or other trigger. This design allows the surgeon to accurately control the laser delivery and make sure the tissue shrinkage is sufficient while avoiding damage to other tissues. In embodiments, triggers, such as finger, hand, foot, toe, etc., can be used to actuate the optical switch/shutter.

Figure 3A:
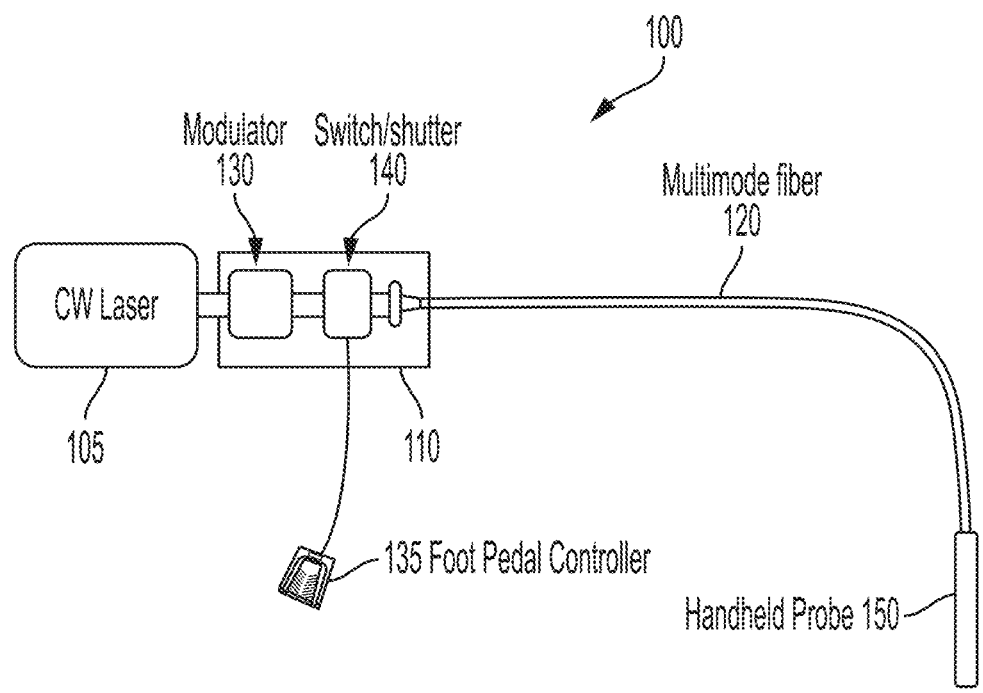
FIG. 3A shows a schematic of a laser thermal conjunctivoplasty system, in accordance with embodiments herein.

FIG. 3A shows a schematic of a system 100 for thermal conjunctivoplasty, in accordance with embodiments herein. In the embodiment shown in FIG. 3A, laser light from a continuous-wave (CW) laser 105 passes through a control unit 110 and is then focused into a multimode fiber 120, which is coupled to a handheld probe 150. Modulator 130 in the control unit converts the continuous-wave (CW) laser light into pulses, thereby providing pulsed laser light. A foot pedal 135 controls the opening and closing of an optical switch/shutter 140 so that the optical switch/shutter 140 is open for a selected period of time (e.g. 2 seconds) to allow the delivery of a fixed number of pulses. The handheld probe 150 delivers laser energy to the conjunctiva.

Figure 3B:
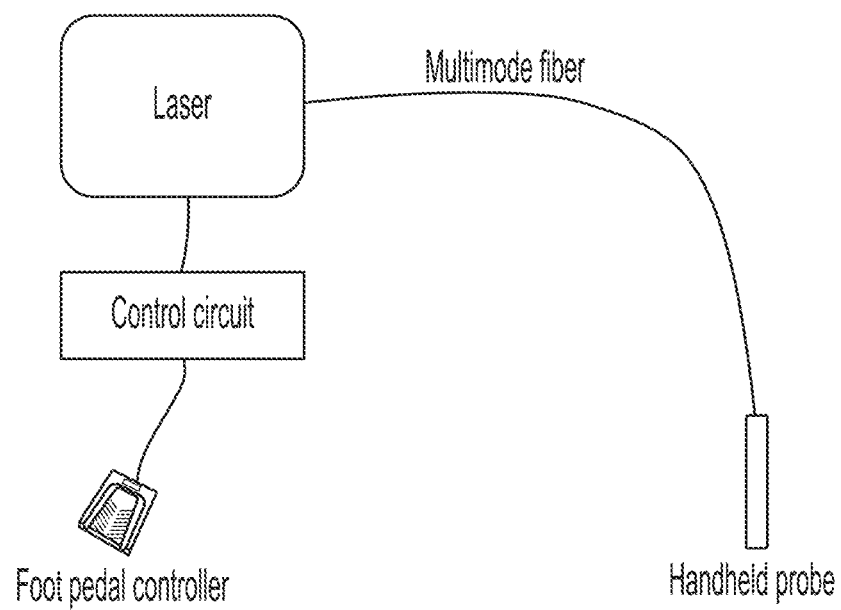
FIG. 3B shows a schematic of a laser thermal conjunctivoplasty system, in accordance with another embodiment herein.

In one embodiment as shown in FIG. 3B, the laser light is controlled through a circuit which is connected to a foot pedal switch. The foot pedal controls the delivery of the laser pulse from the laser source via the circuit. A multimode fiber is connected to the laser source and delivers the laser light into the handheld probe. The handheld probe sends the laser energy to the conjunctiva.

Figure 4A:
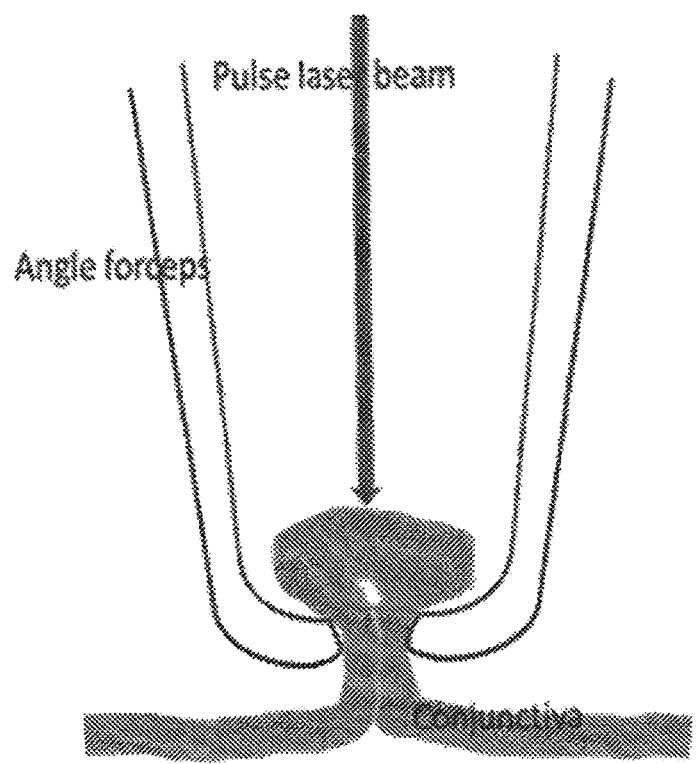
FIGS. 4A-4F are a set of schematics showing: (A) the application of a laser beam on a fold of redundant conjunctival tissue grasped by forceps of a handheld laser conjunctivoplasty probe; in accordance with embodiments herein; (B) light focusing optics of a handheld laser probe; in accordance with embodiments herein; (C) light focusing optics of a handheld laser probe; in accordance with embodiments herein; (D) the ray trace simulation of the embodiment in FIG. 4C. A handheld laser probe receiving laser light through a multimode optical fiber, the output of which is focused by a cylindrical lens into a line; (E), a handheld conjunctivoplasty probe; in accordance with embodiments herein; and (F) a digital image of the handheld conjunctivoplasty probe; in accordance with embodiments herein.

FIG. 4A shows the configuration for laser delivery to redundant conjunctival tissue. A line-focused laser beam is delivered to the conjunctive fold held by a pair of forceps. The laser energy is applied in pulses that confine the peak heating to the conjunctival fold. Since the conjunctiva is approximately 0.24 mm thick as a single layer, the fold held by the forceps would be approximately 0.5 mm. Multiple pulses are delivered to achieve collagen shrinkage, which can be directly visualized by the surgeon. The number of pulses that are delivered to the tissue is controlled by the foot pedal (see FIG. 3).

Figure 4B:
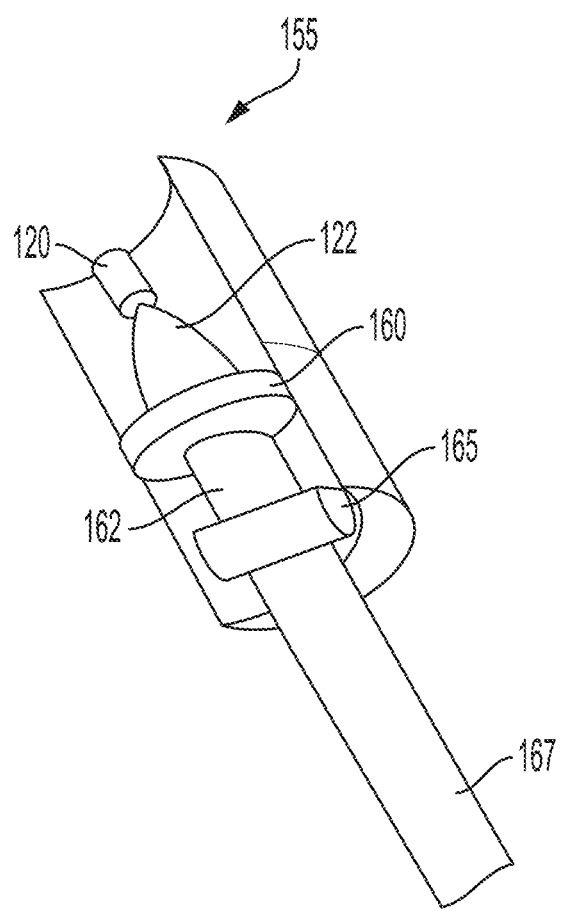

FIG. 4B shows the light focusing optics 155 of the handheld probe, in accordance with embodiments herein.

The light 122 from the multimode fiber 120 is collimated by a collimator 160 to collimated light 162 and then focused by a cylindrical lens 165, for example, to form a line directed laser beam 167. In embodiments, the focal length of the collimator is about 5 to about 20 mm, such as about 10 mm. In embodiments, the numerical aperture of the multimode fiber is form about 0.1 to about 1.0, such as about 0.5. In embodiments, the diameter of the collimated beam after the collimator is from about 5 mm to about 15 mm, such as about 10 mm. In embodiments, the cylindrical lens 165 focuses the collimated beam into a line with a length of about 10 mm (range 5 to 20 mm) and a width of about 1 mm (range 0.5 to 2 mm).

Figure 4C:
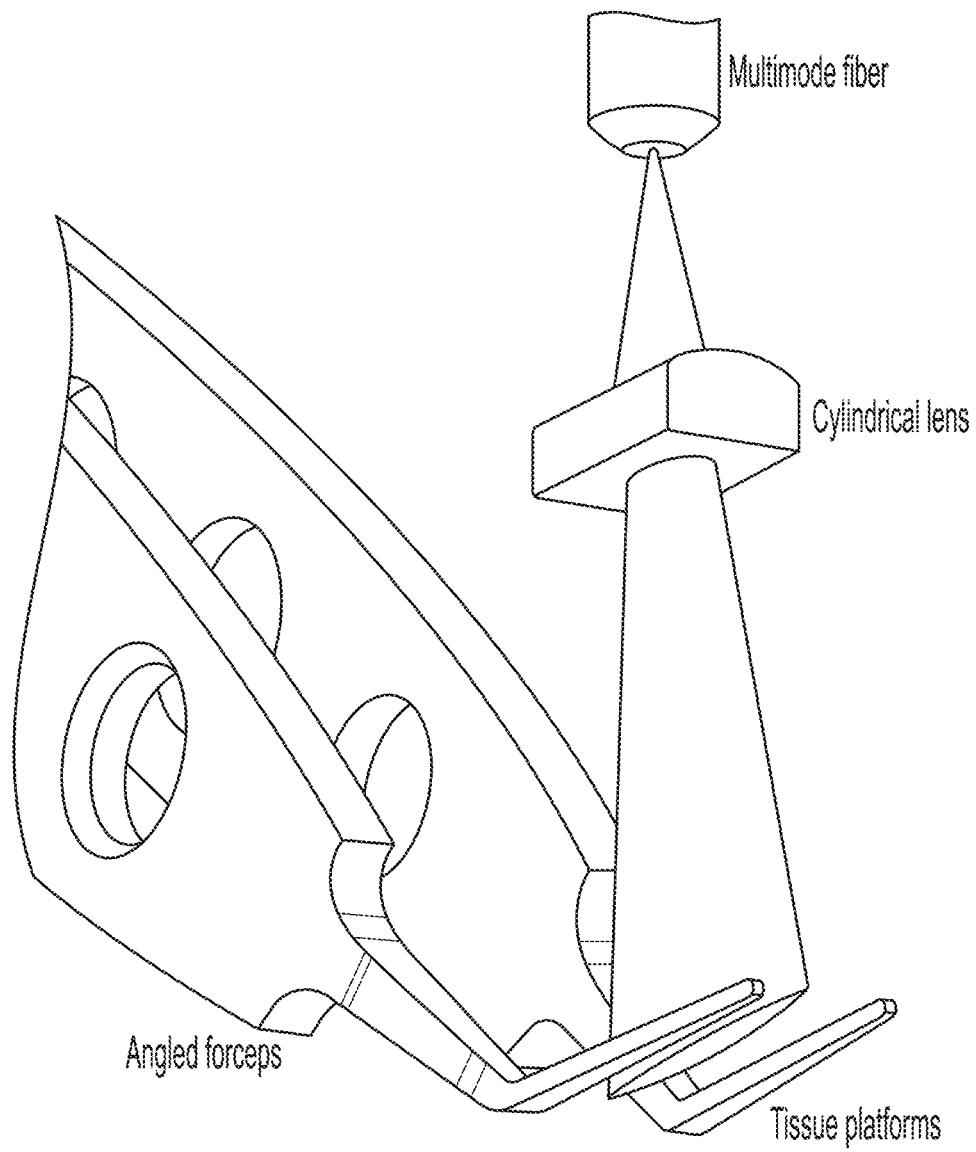

FIG. 4C shows another embodiment of the invention without using the collimator. The light from the multimode fiber directly goes through a cylindrical lens; the light is focused into a line on the conjunctiva tissue with a length of about 10 mm (range 5 to 20 mm) and a width of about 1 mm (range 0.5 to 2 mm).

Figure 4D:
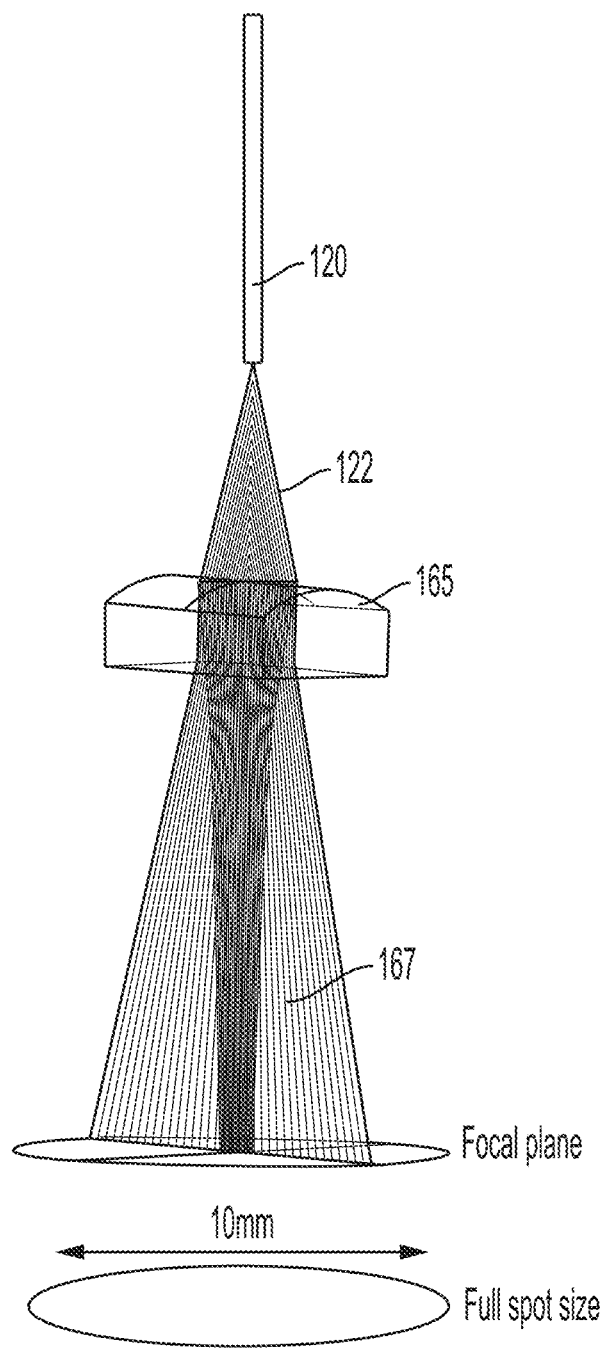

FIG. 4D shows the ray trace simulation of the embodiment in FIG. 4C.

Figure 4E:
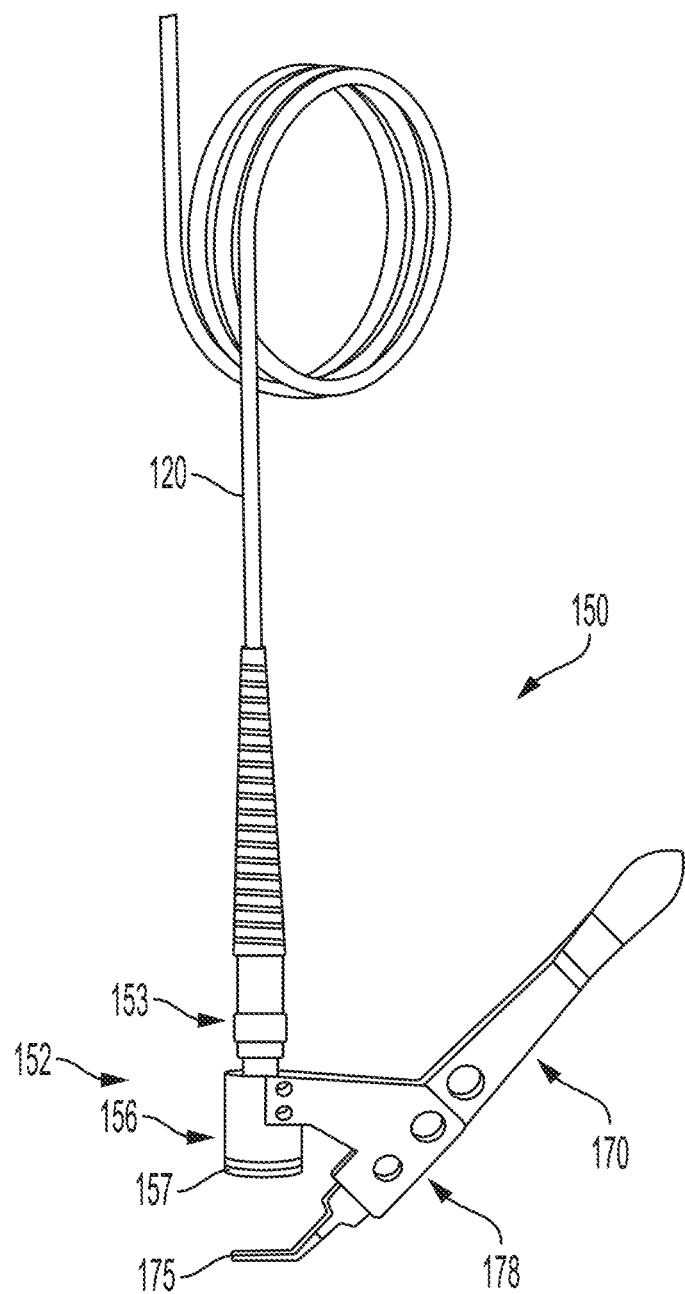

FIG. 4E shows additional details of a handheld laser probe 150. In the embodiment shown, the handheld laser probe 150 receives laser light from the multimode fiber 120, which is connected to the probe through fiber connector, such as an SMA fiber connector. The handheld laser probe 150 may include a housing 152 and forceps 170. In embodiments, forceps 170 are angled at the end proximal to the beam of the laser with long tissue grasping platforms 175. In embodiments, the housing 152 includes a mechanical holder, such as connecting struts 178 to couple to the forceps 170. In the embodiment shown, the housing 152 includes a fiber adapter 153 to couple the multimode fiber 120 to the housing 152. The housing 152 also includes a seal ring 157 for fastening a lens in the lens holder 156.

Figure 4F:
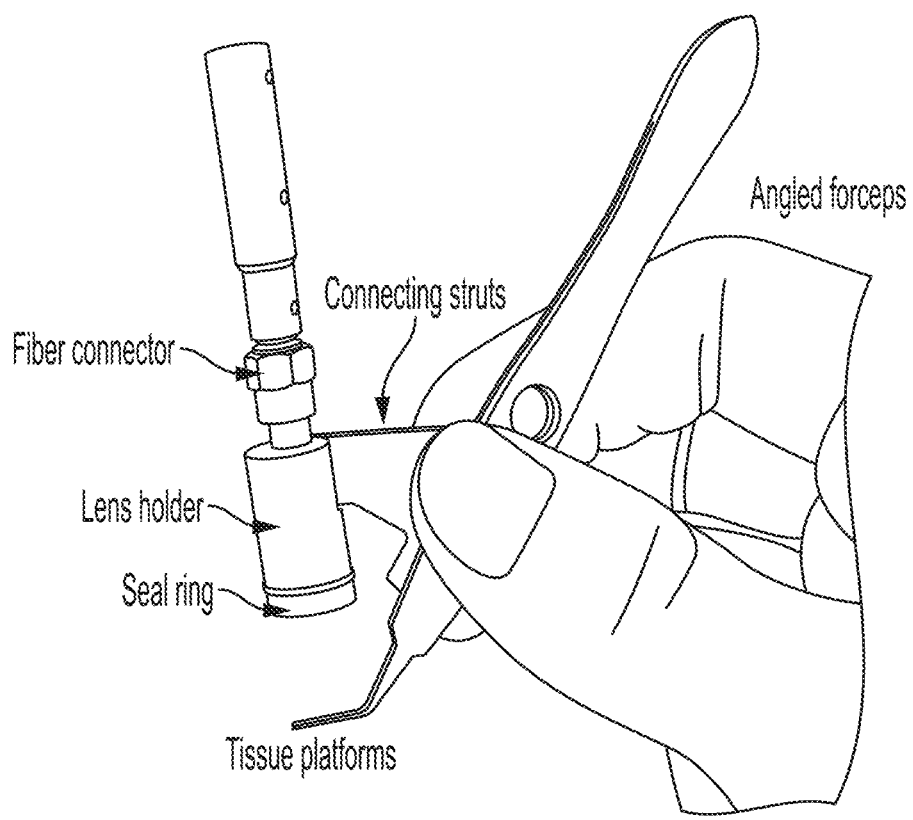

FIG. 4F shows a photograph of the handheld probe held in hand.

Aspects of the current disclosure relate to methods of laser thermal conjunctivoplasty. The disclosed methods include delivering laser light from a handheld laser probe to a conjunctiva fold, such as a handheld laser probe including a pair of forceps as disclosed herein. One of the unique aspects of the disclosed methods is that they can easily be done in clinic at a slit-lamp biomicroscope or in a minor procedure room under an operating microscope.

As disclosed herein, the devices, systems and methods use the heating of the water within conjunctival tissue produced by a laser light. To heat water in the conjunctival tissue to shrink its full thickness, but no deeper heating than necessary, the laser pulse duration, duty cycle, and power, can be optimized. While not being bound by theory, a laser beam focused into a line on the conjunctival tissue can be modeled as a one-dimensional heat diffusion problem for the calculation of tissue thermal relaxation time:

$$\tau = \frac{d^2}{4D} \qquad (1)$$

where $\tau$ is the thermal relaxation time, D is the heat diffusivity, and d is the heat diffusive length of tissue.

The heat diffusivity is approximately $1.3 \times 10^{-7}$ m$^2$ s$^{-1}$. For a conjunctiva fold thickness of 0.5 mm, the thermal relaxation time is about 0.48 second. Thus, the pulse duration of the laser should be set to be shorter than about 0.48 second to prevent peak temperature from diffusing more than 0.5 mm deeper than the depth at which the laser energy is absorbed.

In embodiments, the methods include grasping the conjunctiva fold with the forceps and lifting the conjunctival fold off the sclera and thereby minimizing the chance of damaging the underlying sclera, ciliary body, choroid, and retina.

Figure 5:
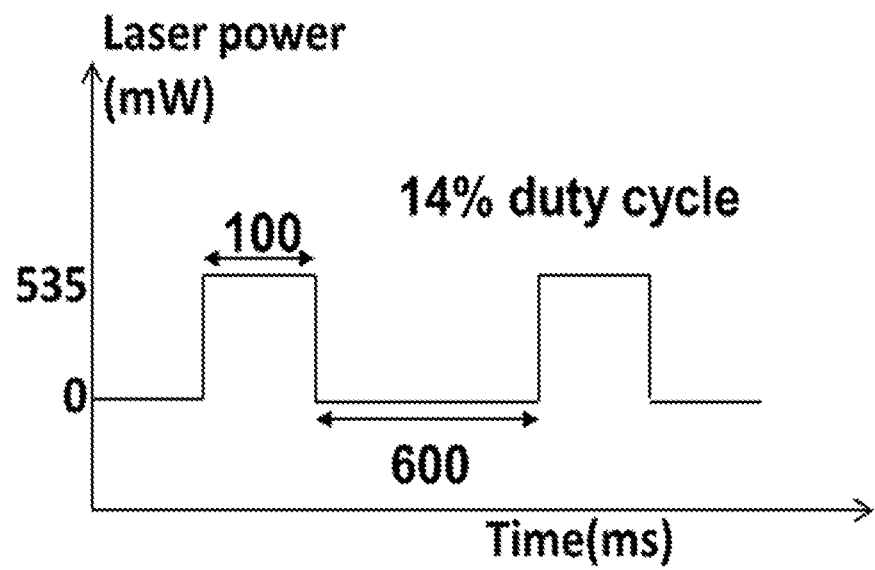
FIG. 5 is a graph of a laser pulse time profile.

In embodiments, the laser light source is a pulsed laser. FIG. 5 shows the schematic of an example laser pulse. The low duty cycle allows ample time for heat dissipation in deeper tissue to minimize collateral damage.

Assuming that the pulse is short enough for adiabatic heating, the energy absorbed by the tissue is calculated as:

$$\psi(z) = \psi_0 e^{-\mu_a z} \qquad (2)$$

where $\psi_0$ is the laser fluence, $\mu_a$ is the absorption coefficient of water, the dominant absorber at the wavelength used. So the energy density inside the tissue can be described as:

$$\mu_a \psi_0 e^{-\mu_a z} \qquad (3)$$

Figure 6:
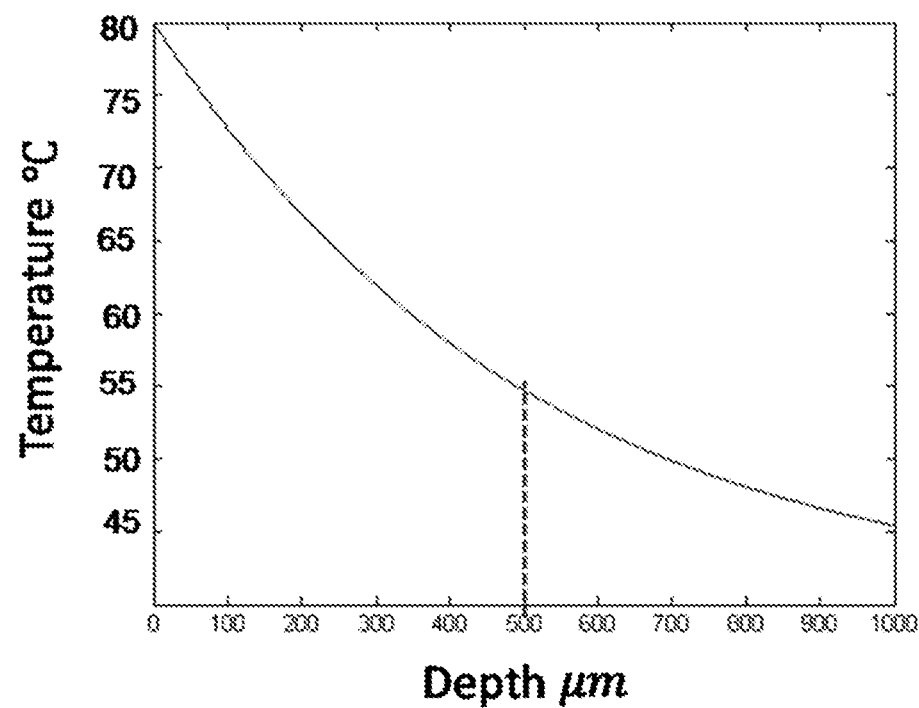
FIG. 6 is a graph of a simulated temperature profile inside the conjunctiva.

The temperature increase inside the tissue will be:

$$\Delta T = \mu_a \psi_0 e^{-\mu_a z} / \gamma \rho s \qquad (4)$$

where $\gamma$ is the water content fraction in tissue, $\rho$ is the mass density of water and s is the heat capacity of water. The water content of the conjunctiva is assumed to be 80%, the mass density of water is 1000 Kgm$^3$ and the heat capacity of water is 4350 J·Kg$^{-1\circ}$ K$^{-1}$. FIG. 6 shows the theoretical temperature inside the conjunctiva tissue based on a laser pulse duration of 125 ms, a repetition rate of 1.5 Hz and laser power of 535 mW. Within a depth of 0.5 mm (thickness of a conjunctival fold), the temperature varied between 55-80° C. after the heating. This temperature range is ideal for shrinking conjunctival collagen.

In embodiments, the laser light is focused into a line with a length of 10 mm and a width of 1 mm.

EXAMPLES

Example 1

Ex Vivo Experiment to Optimize Laser Parameters

Ex-vivo eyes, for example porcine, bovine, or human eyes, may be used to assess thermal shrinkage of the conjunctiva. For example, different laser energies (for example, between 0.1 and 6.0 W), pulse durations (for example, between 100 and 300 milliseconds), and repetition rates (for example, between 0.5 and 3 Hz) may be investigated to characterize and optimize the performance the disclosed laser thermal conjunctivoplasty (LTC) systems and methods. Optical Coherence Tomography (OCT) images may be used to evaluate the results. Experimental treatment may be characterized by measuring the shrinkage of conjunctival tissue as measured across the width of the laser heating line and/or by the absence of mechanical disruption of the treated conjunctiva or underlying tissue. Within such a framework, experimental treatment may be judged to be successful if a threshold of shrinkage expressed as a percentage change in width is achieved, for example, 50% or greater change in width. An example of such an experiment using ex vivo porcine eyes is described below.

Figure 7A:
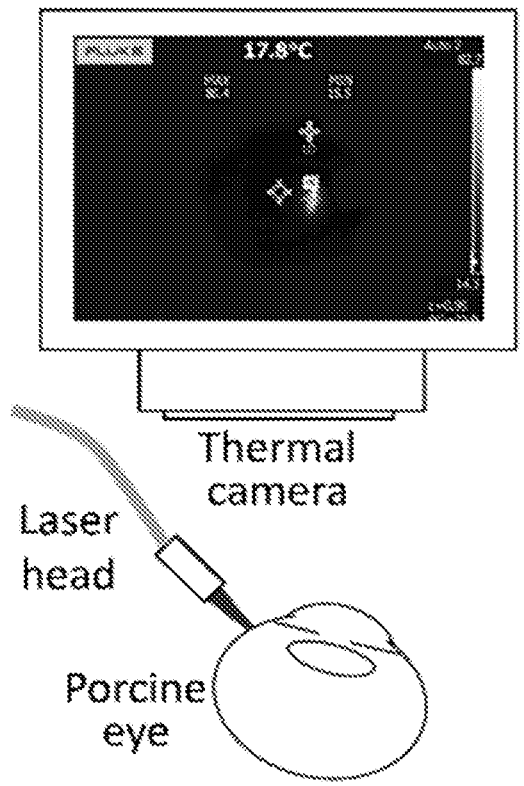
FIGS. 7A-7C are a set of schematics showing: (A) a setup for measuring laser-induced temperature variation using a thermal camera; (B) a setup for recording the dynamic shrinkage process by a 1310-nm optical coherence tomography system; and (C) a procedure to measure the shrinkage from the LTC.
Figure 7B:
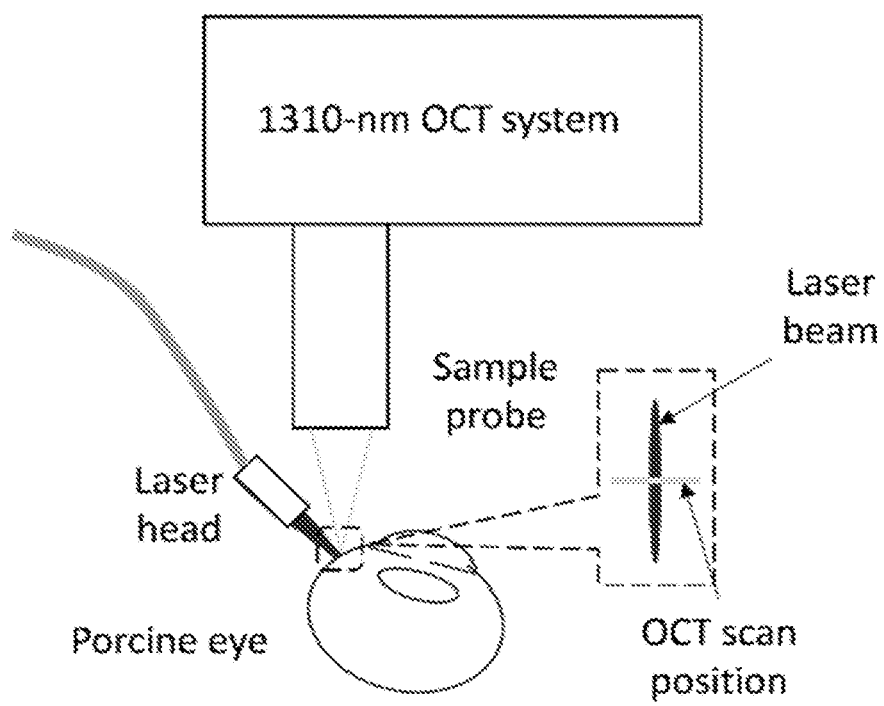
Figure 7C:
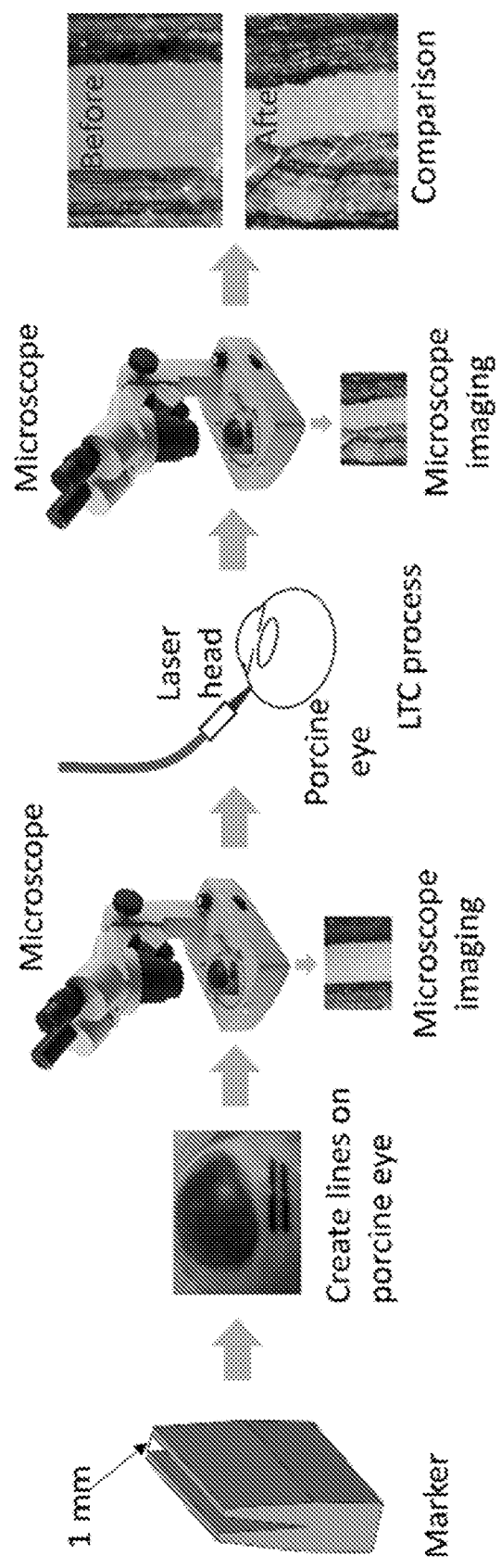

Ex-vivo porcine eyes were used to assess thermal shrinkage of the conjunctiva, to optimize the laser parameters, and to verify the NIR LTC performance. A thermal camera (TiS45, Fluke, Everett, Wash., USA) was used to record the temperature change of the region over time during the LTC. OCT was also used to monitor the tissue structural change during the experiment. FIG. 7A shows the experimental setup for LTC of a porcine eye (bottom part of figure) and a representative thermal camera image (top part of figure). The thermal camera allows the recording of images during LTC such that the temporal changes in temperature can be obtained with a resolution of 33 ms. A custom 1310-nm swept-source OCT system with an A-line rate of 50 kHz, a transverse resolution of 15 µm, and an axial resolution of 8.5 µm was used to monitor the LCT process. FIG. 7B shows a schematic of the OCT aspect of the experiment. The OCT B-scan covered a range of 5 mm and repeated B-scans at the same location were recorded. The OCT frame rate was 50 Hz. The laser-induced shrinkage was measured using the workflow depicted in FIG. 7C. A 3D-printed marker was used to create two parallel lines, 10 mm in length and separated by 1 mm, on the conjunctiva. A photo of the targeted area was taken using a digital microscope (OMAX, Gyeonggi-do, Korea). The marked region was treated with NIR LTC and a second photo was taken with the microscope. The shrinkage percentage of the region was calculated from the two photos taken before and after LTC.

Figure 8A:
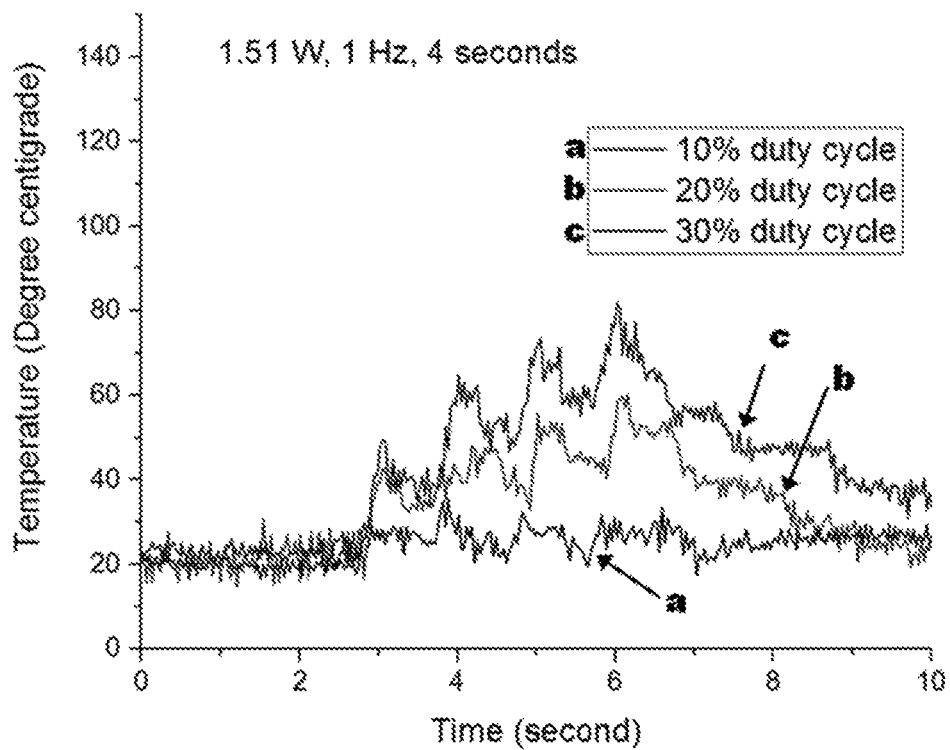
FIG. 8A is a graph of the temperature changes recorded in tissue during a 1.51 W peak power LTC experiment at three different duty cycle settings.
Figure 8B:
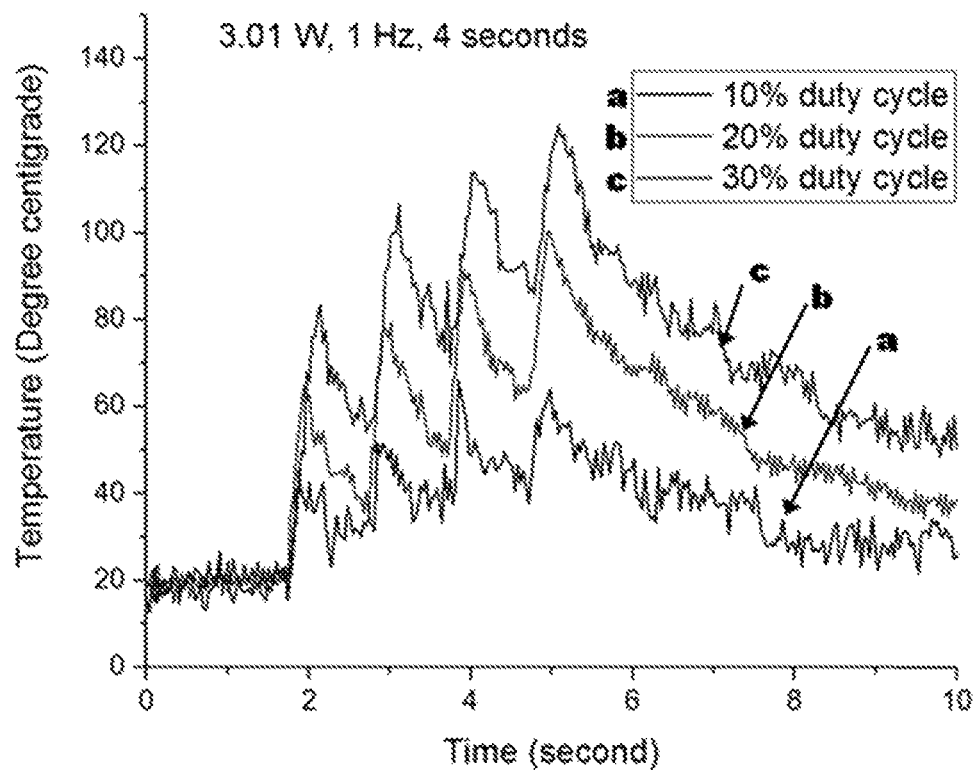
FIG. 8B is a graph of the temperature changes recorded in tissue during a 3.01 W peak power LTC experiment at three different duty cycle settings.

FIG. 8A and FIG. 8B show the temporal changes in temperature during the LTC experiment as measured by the thermal camera. The highest valued temperatures in each of recorded thermal camera image sequences were obtained and plotted versus time. As can be seen from FIG. 8A and FIG. 8B, the peak temperature increases rapidly during the laser pulse illumination period and then decreases relatively slowly during the period when the laser is off. Three different peak laser powers and pulse duty cycles were investigated. Room temperature was held at ~20° C. during the duration of the experiments. At a laser peak power of 1.51 W and 10% duty cycle (100 ms pulse duration), the observed temperature increases during laser illumination were very small, with the temperature never exceeding 40° C. (FIG. 8A). When the duty cycle was increased to 20% (200 ms pulse duration) and 30% (330 ms pulse duration), the cumulative effect of multiple pulses were clearly seen. Each laser pulse induced a temperature increase during the illumination period and a temperature decrease during the laser-off period. This temperature increase-decrease cycle caused a sustained increase in successive peak temperatures attained with each successive pulse. For a peak power of 3 W, the maximum temperature for the 30% duty cycle exceeded 100° C. while the maximum temperature for the 10% duty cycle was approximately 65° C. (FIG. 8B). When the peak power was increased to 5.77 W, the maximum temperature exceeded 100° C. for all three duty cycles (temperature data not shown).

Figure 9A:
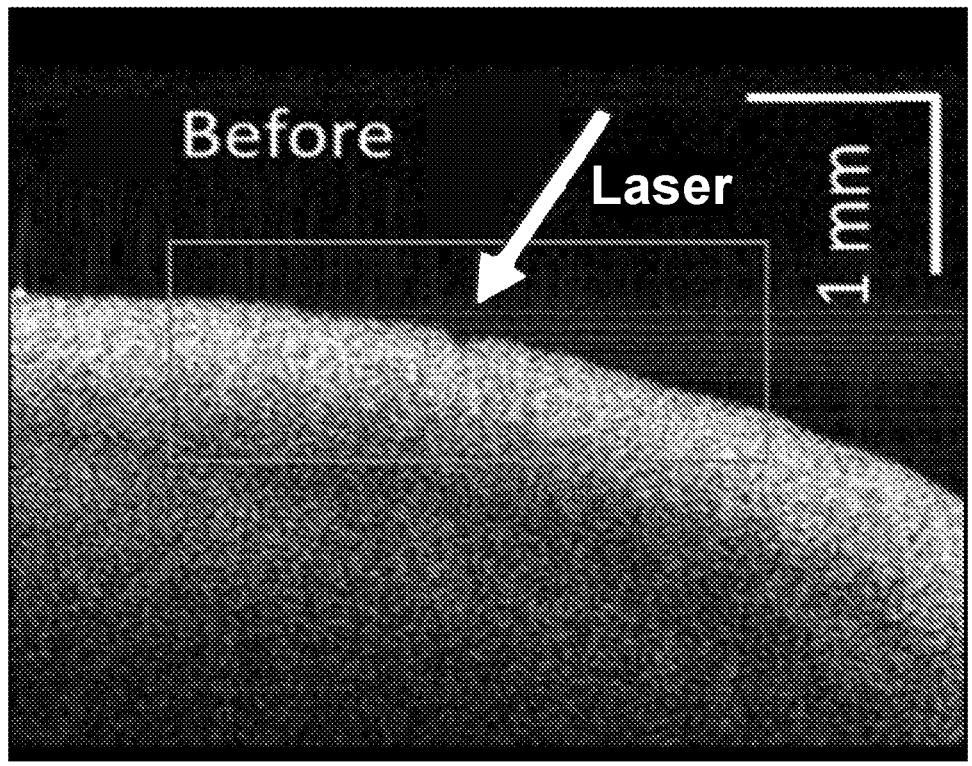
FIGS. 9A-9B are a set of OCT B-frames showing: (A) the tissue configuration before LCT with a rectangular box delineating the region of interest for particle image velocimetry analysis; and (B) the tissue configuration after LTC with a rectangular box delineating the region of interest for particle image velocimetry analysis.
Figure 9B:
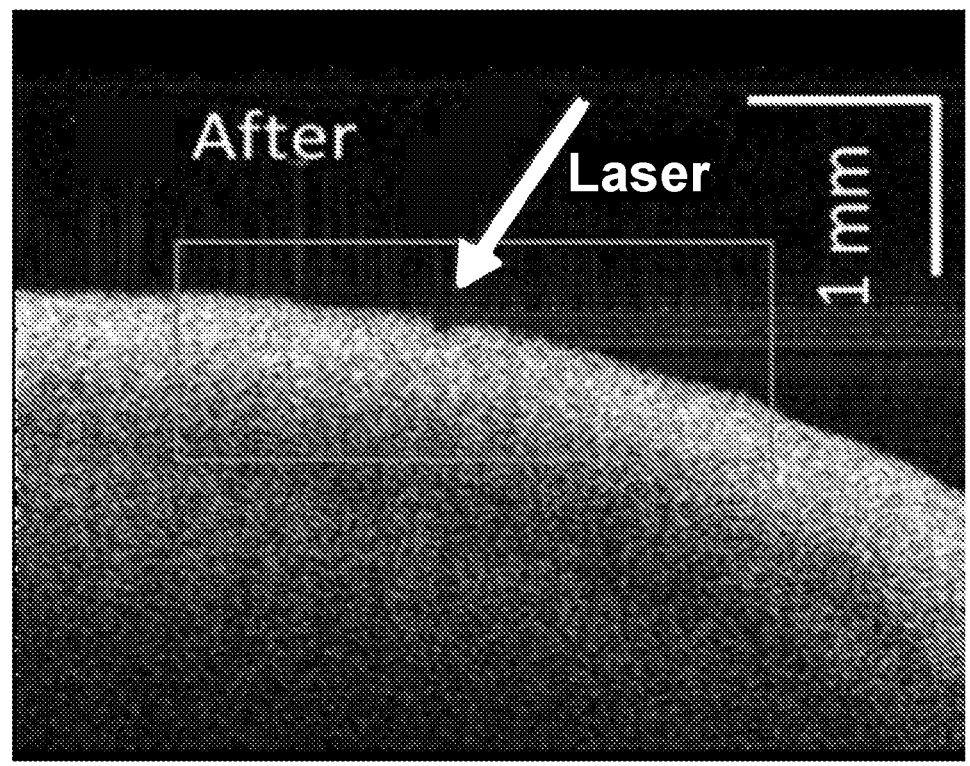
Figure 9C:
FIG. 9C is an image showing particle image velocimetry results obtained from analysis of the regions bounded by the rectangular boxes in FIGS. 9A and 9B.

Real-time OCT imaging was used to monitor the LTC-induced shrinkage process. This dynamic process can be clearly visualized using time-sequence images from OCT B-scans. FIG. 9A and FIG. 9B show exemplary OCT images before and after LTC, respectively. To quantify the shrinkage during the LTC, particle image velocimetry (PIV) was employed to analyze tissue deformation as captured by the OCT B-scan images. FIG. 9A and FIG. 9B show the region of interest (denoted by a rectangular box) encompassing image pixels used to calculate PIV maps. The software program ImageJ was used to perform the PIV calculation. The results of the PIV calculation are shown in FIG. 9C. As shown, the direction and speed of tissue movement are represented by oriented arrows within the rectangular region of interest, with the arrows sized smaller to larger to represent lower and higher local speed magnitudes, respectively. Local speed magnitude is further coded by a grayscale gradient as represented in the vertical scale bar of FIG. 9C. In the experimental mapping depicted here, the large arrow groups at the left and right ends of the region of interest are directed centrally towards the location of laser-induced heating. This mapping indicates that a shrinkage process is taking place to draw surrounding tissue towards the site of targeted laser heating.

Figure 10:
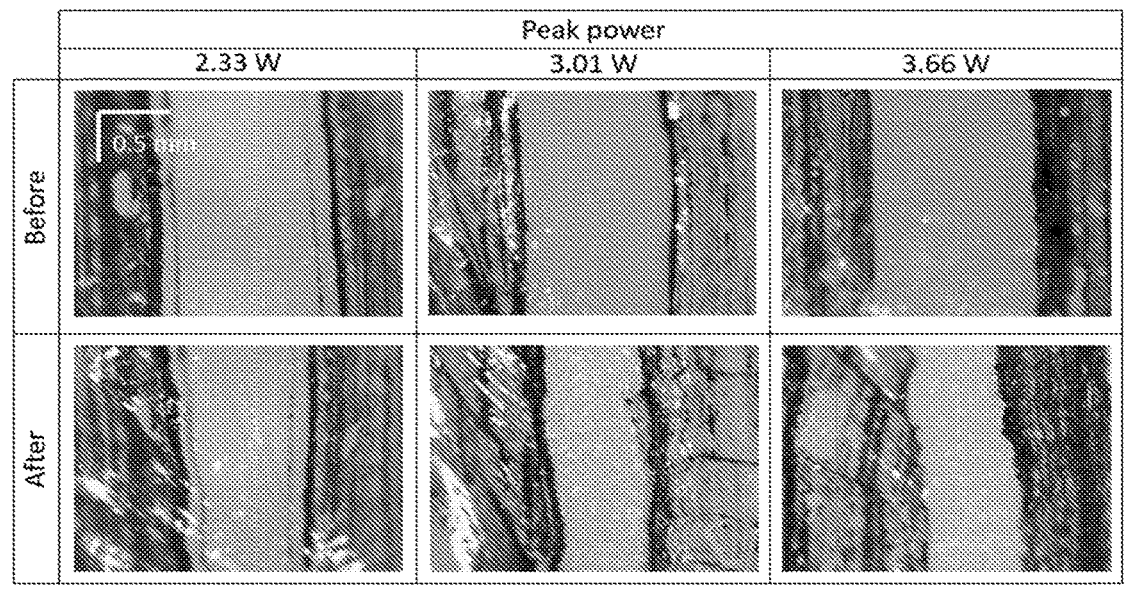
FIG. 10 is a panel of photomicrographs of the treated regions of the porcine eyes before and after LTC with different laser peak power values. The duty cycle is set at 20%. The dark regions on the left and right of each photomicrograph are the marks from the tissue marker. The top row shows the photographs before LTC and the corresponding photographs after the LTC are shown in the bottom row.

The influence of different laser parameters on the shrinkage was also investigated. FIG. 10 shows a panel of microscope images of porcine eyes before and after LTC treatment at laser peak powers of 2.33 W, 3.1 W, and 3.66 W. The pulse duty cycle in this experiment was set to 20%. As demonstrated, the amount of shrinkage increases as the laser peak power increases. For the peak power of 2.33 W, the shrinkage is about 21%. When the peak power is increased to 3.01 W and 3.66 W, the shrinkage increases to about 36% and about 45%, respectively.

Figure 11:
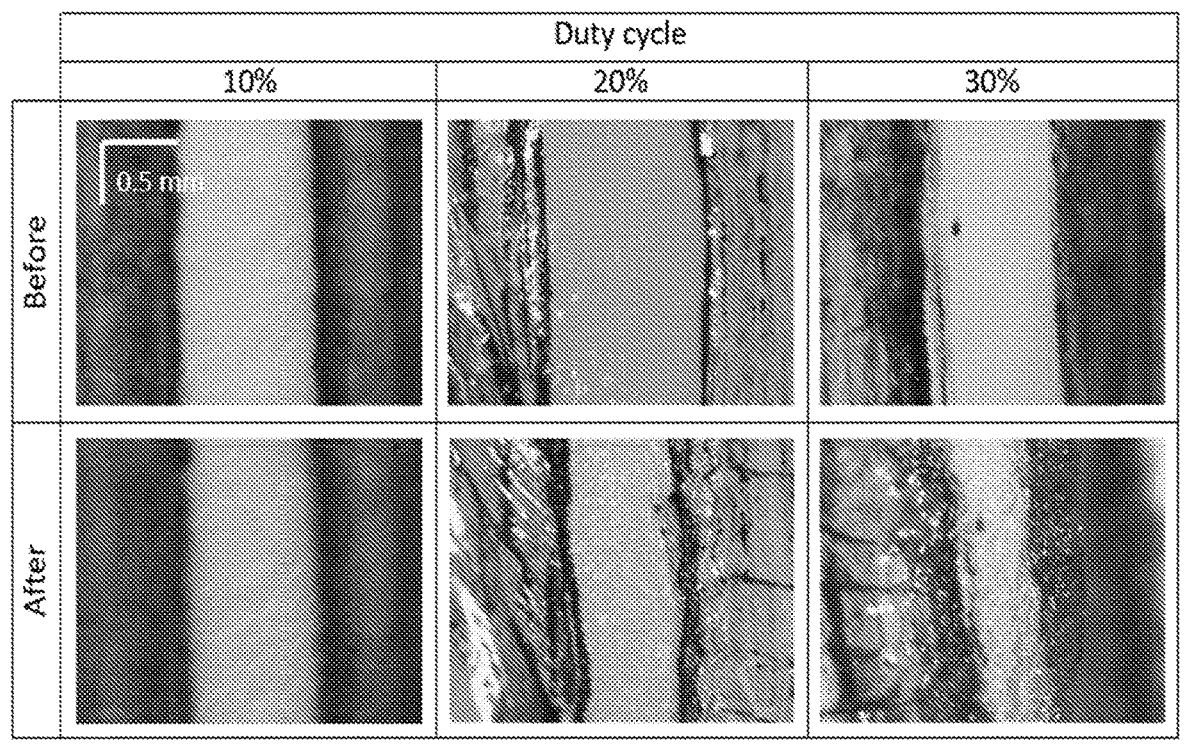
FIG. 11 is a panel of photomicrographs of the treated regions of the porcine eyes before and after LTC with different pulse duty cycle values and a peak power of 3 W. The top row shows the photographs before LTC and the corresponding photographs after the LTC are shown in the bottom row.

The experiments described above indicate that a 3.01 W peak power and 20% duty cycle provides a favorable amount of tissue shrinkage without inducing injurious temperature levels (the measured temperature is about 88° C. in the tissue for these parameter values). This peak power (3.01 W) was employed to further investigate the influence of the pulse duty cycle on tissue shrinkage. FIG. 11 shows a panel of microscope images of tissue shrinkage using a pulse duty cycles of 10%, 20% and 30%. As can be seen from these images, at a duty cycle of 10%, the tissue shrinkage is minimal (about 8%). When the duty cycle is increased to 30%, the tissue shrinkage is about 45%. However, a 3.01-W peak power and 30% duty cycle combination also damages the surface of the tissue due to excessive temperature induction (the surface temperature was measured to reach about 116° C. for these parameter values).

Figure 12A:
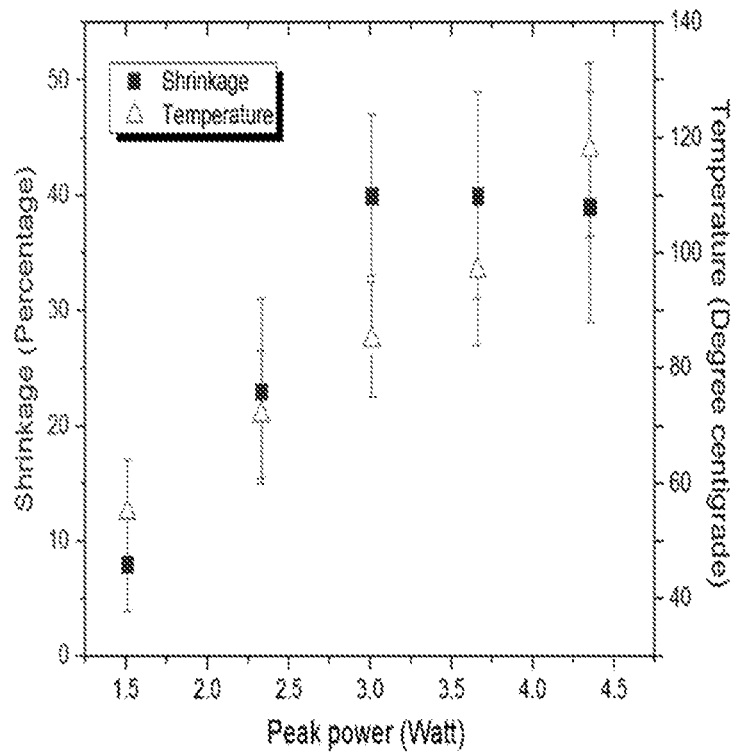
FIG. 12A is a graph showing shrinkage and temperature as a function of laser peak power. The pulse laser duty cycle is set at 20%. The shrinkage rate saturates with the increase of the peak power and the temperature continues to increase with the increase of the peak power.
Figure 12B:
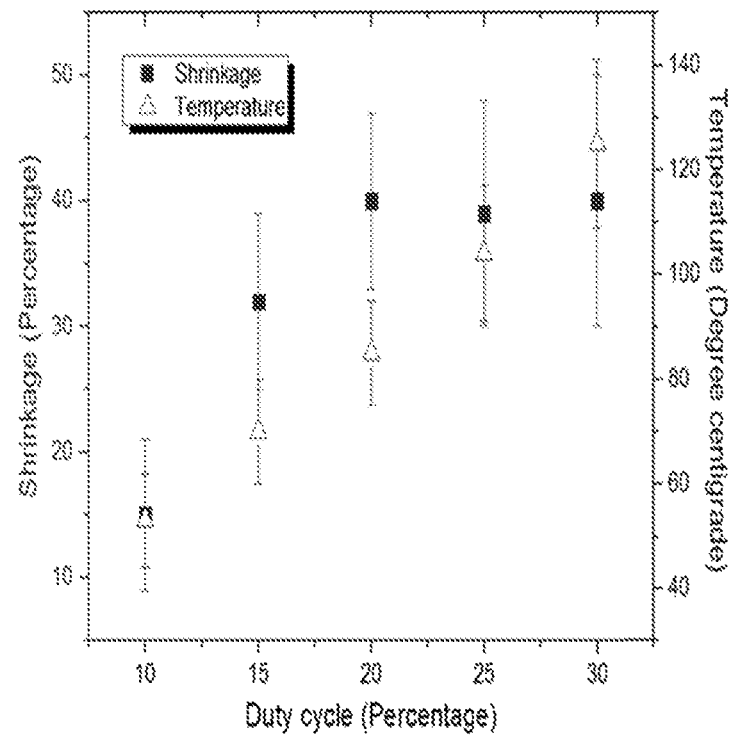
FIG. 12B is a graph showing shrinkage and temperature as a function of pulse duty cycle. The laser peak power was set at 3 W. The shrinkage rate saturates with the increase of the duty cycle and the temperature continues to increase with the increase of the duty cycle.

Experiments were also conducted to characterize the relationship between tissue shrinkage and tissue temperature for different laser parameters combinations (in this case, laser peak power and duty cycle). For each specific laser parameter combination, the tissue shrinkage and temperature was measured 6 to 8 times on different samples and the results averaged. FIG. 12A shows the tissue shrinkage and temperature as a function of laser peak power using a default duty cycle of 20%. As shown, tissue temperature increases as the peak power increases while the amount of tissue shrinkage saturates at a peak power of 3 W and higher. This suggests that a peak power of about 3 W is well-suited to LTC applications, but that higher peak power levels do not confer additional beneficial shrinkage effect. FIG. 12B shows tissue shrinkage and temperature as a function of pulse duty cycle using a peak power of 3 W. As shown, when the duty cycle is set at 30% the tissue temperature rises well above 110° C. while the amount of tissue shrinkage is comparable to that obtained using a 20% duty cycle.

Based on these experimental results obtained using an exemplary 1460-nm laser system and handheld line-focused laser probe (for example, as described in Example 3 below), in an embodiment, an optimized set of LTC surgery laser parameters comprises a laser signal having 3-W peak power, 1-Hz repetition rate, 20% duty cycle and 4-seconds work duration. The resultant tissue shrinkage obtained using this parameter set in the experimental setting described herein was about 40%.

Figure 13:
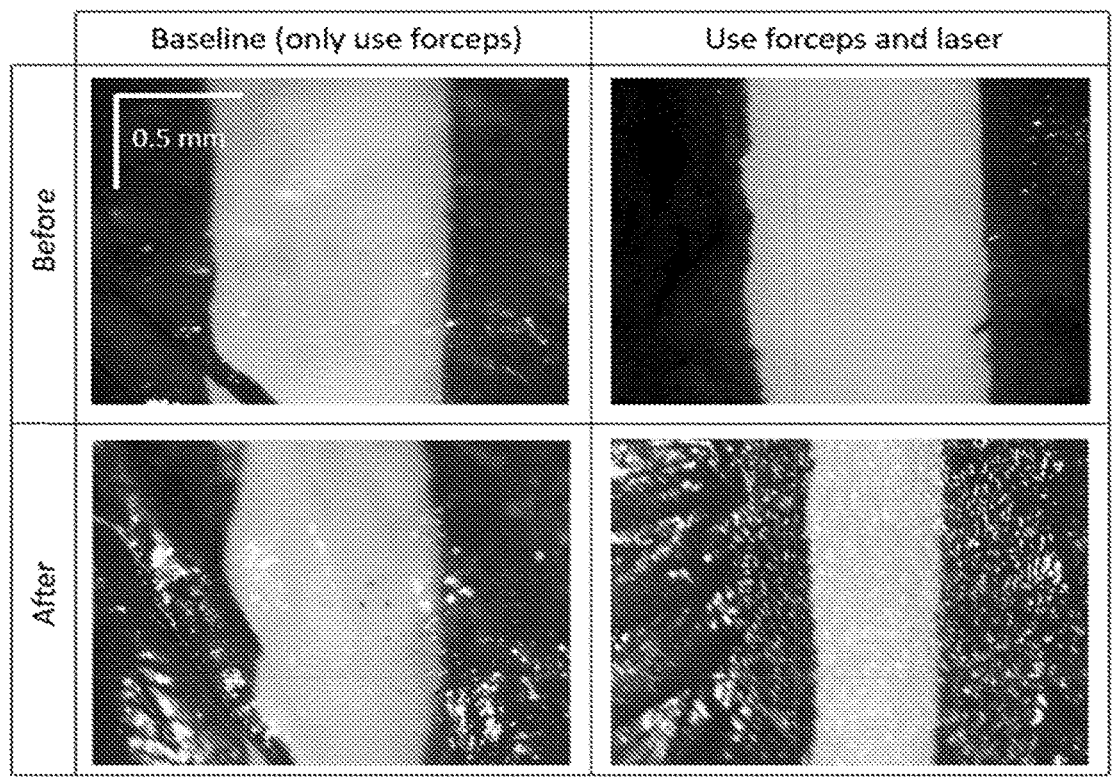
FIG. 13 is a panel of photomicrographs showing tissue shrinkage results using only the forceps or both the forceps and the laser.

Further experiments were performed to determine the extent to which grasping the conjunctival tissue between the forceps during treatment contributes to tissue shrinkage via mechanically-induced permanent deformation. In embodiments, the device is designed to work with angled forceps such that the working distance from the cylindrical lens to the tissue platforms is constant, the incident laser angle is normal to the tissue surface, and only the tissue fold held by the forceps is heated. However, because the forceps impart a mechanical force to the tissue while holding it, it is possible that a permanent or transient mechanical deformation is induced in said tissue along with thermally-induced deformation (shrinkage) caused by LTC. To quantify the contribution of the forceps' mechanical force on tissue deformation, a test was performed wherein tissue was held in the forceps but not exposed to laser light cycling. The distance change between the parallel maker lines was measured as described earlier. As shown in the left panels of FIG. 13, a change of ~10% between the marker lines was found when mechanical force alone was applied. After the LTC (combined mechanical force and tissue heating), the shrinkage as measure by the change between the marker lines was found to be about 45% (right panels of FIG. 13)

Example 2

In Vivo Animal Wound Healing Experiments

Figure 14:
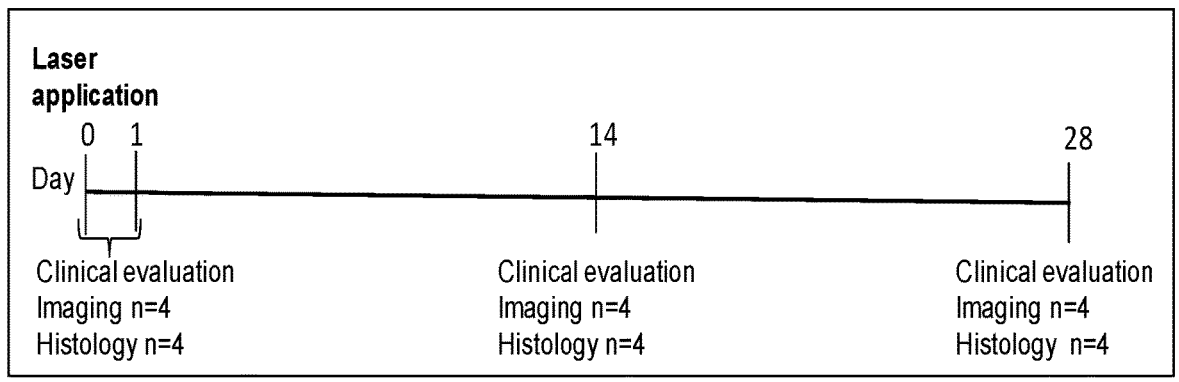
FIG. 14 is a graphic outline of an in vivo animal study for laser thermal conjunctivoplasty.

In vivo animal experiments provide preliminary information on the efficacy and safety of the Laser Thermal Conjunctivoplasty (LTC) procedure. LTC using two different energy settings are performed on the inferior bulbar conjunctiva of one eye of rats that are followed for up to one month after the procedure. The rats are evaluated clinically and by OCT on days 0, 1, 14 and 28 after the procedure (see FIG. 14). The amount of conjunctival shrinkage is measured immediately after the procedure, by measuring the distance between preplaced marks above and below the treatment area. OCT images are taken to evaluate the changes in conjunctival thickness and surface smoothness. The clinical evaluation assesses the degree of conjunctival hyperemia (a measure of inflammation), hemorrhage (bleeding inside tissue), and blanching (a measure of ischemia), if they exist. Digital photography is taken of the eyes before and after staining with fluorescein dye, immediately after the procedure and every 2 days, up to day 8. The photographs document the clinical appearance and fluorescein staining provides measurement of the area of epithelial defect. A randomly designated subset of rats is sacrificed at days 0, 1, 14, and 28, and the treated eyes are removed and embedded in paraffin for histochemical staining to evaluate effects of the laser energy on the conjunctiva and underlying tissues. Eyes are also embedded for preparing frozen sections that are immunostained for epithelial and fibroblast markers to evaluate and compare the wound healing reaction to the different laser energy levels. These parameters are compared to treatment of the superior bulbar conjunctiva with the standard hot wire thermal cautery method to burn/shrink conjunctiva.

Example 3

Exemplary 1460-Nm Programmable Laser Diode System for LCT

Figure 15A:
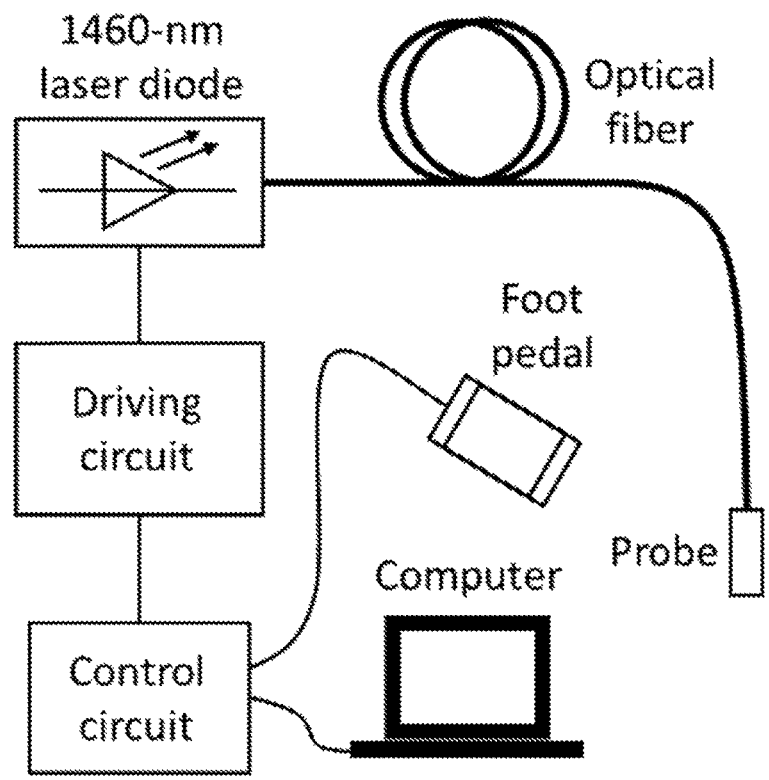
FIG. 15A is a schematic of a 1460-nm LTC system, in accordance with an embodiment herein.

FIG. 15A shows an exemplary schematic of a programmable pulsed laser diode system for use in LTC. In this exemplary embodiment, a fiber-coupled high-power laser diode module with a maximum continuous-wave (CW) power of 12 W (M1F2S22-1470.10-12C-SS5.x, DILAS, Tucson, Ariz., USA) is employed as the light source. The light is output through a multimode fiber with a core diameter of 200 µm and a numerical aperture (NA) of 0.22. The other end of the fiber is connected to a handheld probe. A 650-nm laser diode is integrated into the source laser for aiming purpose. The power for the aiming light is 200 µW.

Figure 15B:
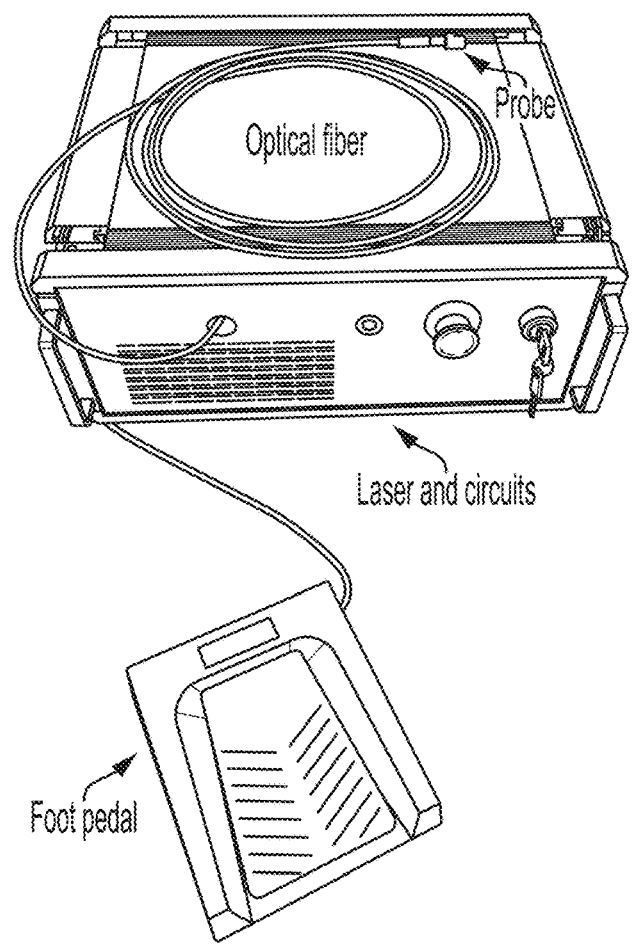
FIG. 15B is a photograph of a prototype LTC system, in accordance with an embodiment herein.

Custom built control circuits are used to drive the 1460-nm laser module. The pulse duty cycle, repetition rate, output power, and working duration are tunable through a programmable control software interface. A 650-nm aiming light can be enabled and disabled by the operator from the control software. A foot pedal is used as a trigger for the laser output. The laser pulse duty cycle, repetition rate, output power, and working duration (or the number of pulses) are preset by the control software. Once the laser output is triggered, the 650-nm aiming light is turned off automatically and the 1460-nm laser is delivered to the probe according to the preset parameters. However, if the foot pedal is released during the procedure, the infrared laser is turned off immediately. A photograph of an exemplary prototype LTC laser system is shown in FIG. 15B. In the embodiment shown, the laser system is assembled into a case having dimensions of 41×36×15 $cm^3$.

Figure 16A:
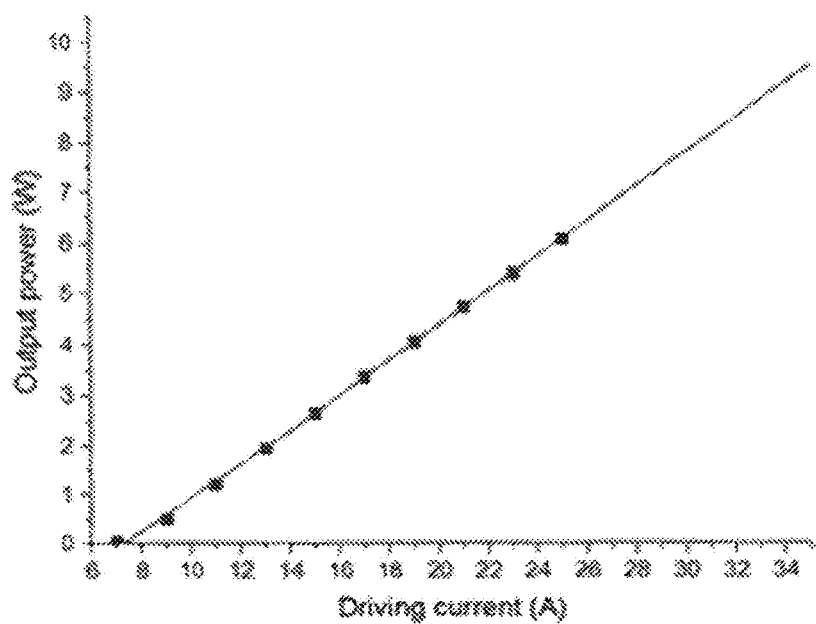
FIGS. 16A-16D is a set of graphs for a prototype 1460-nm diode laser system showing: (A) the proportionality between output power and the driving current; (B) the laser output spectrum at different output powers; (C) the temporal characteristics of the output pulse intensity for different pulse widths; and (D) the output pulse trains with different pulse numbers.
Figure 16B:
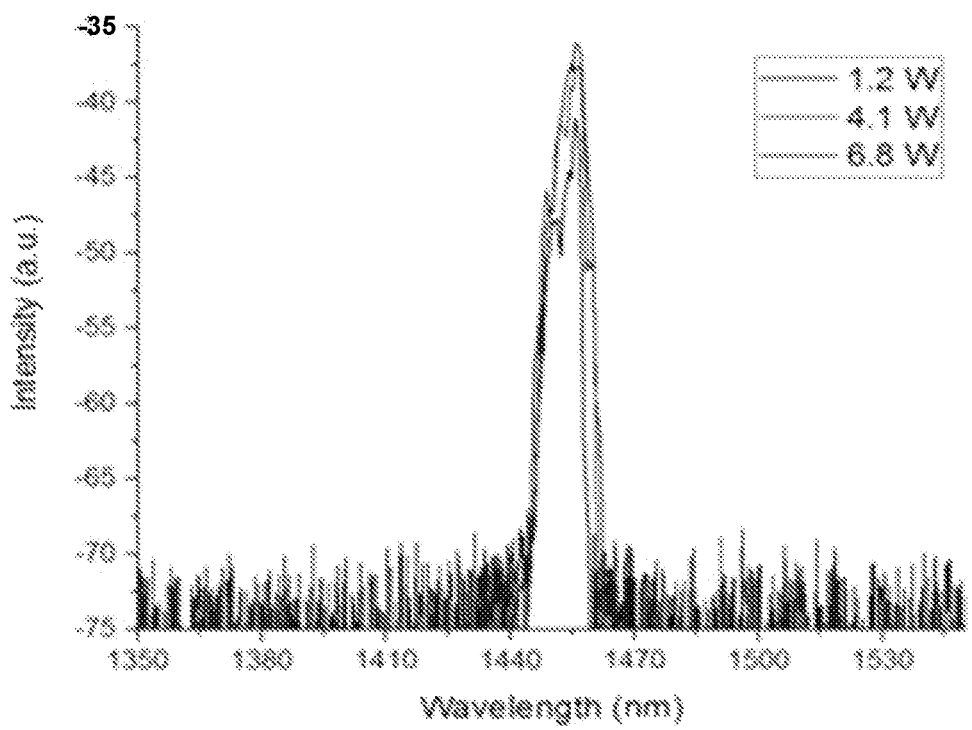
Figure 16C:
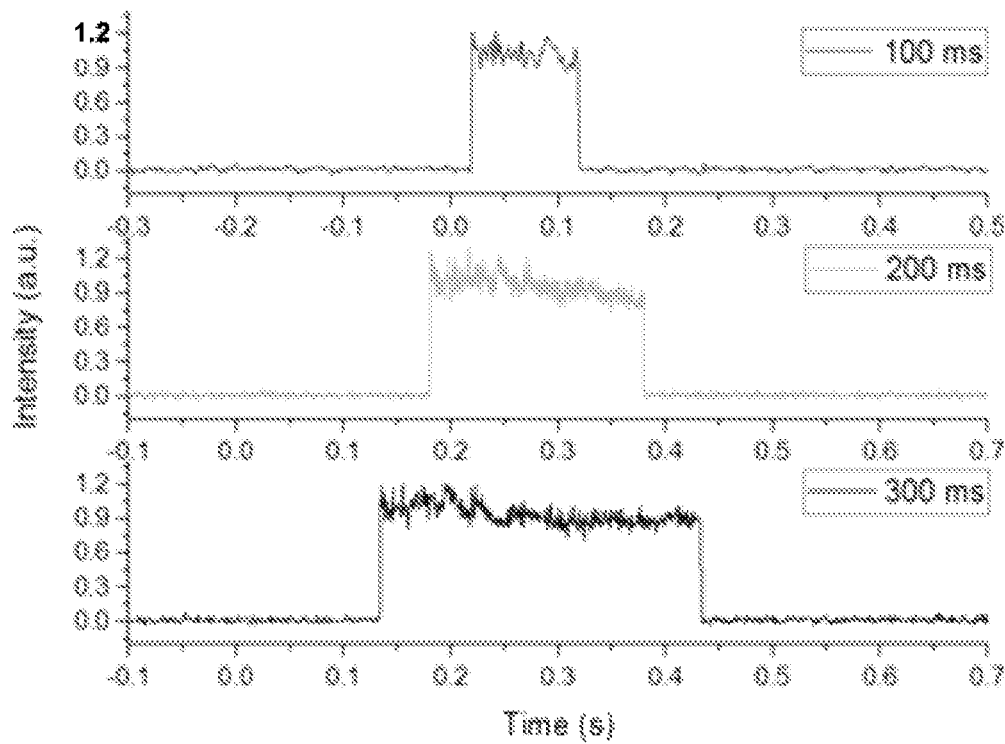
Figure 16D:
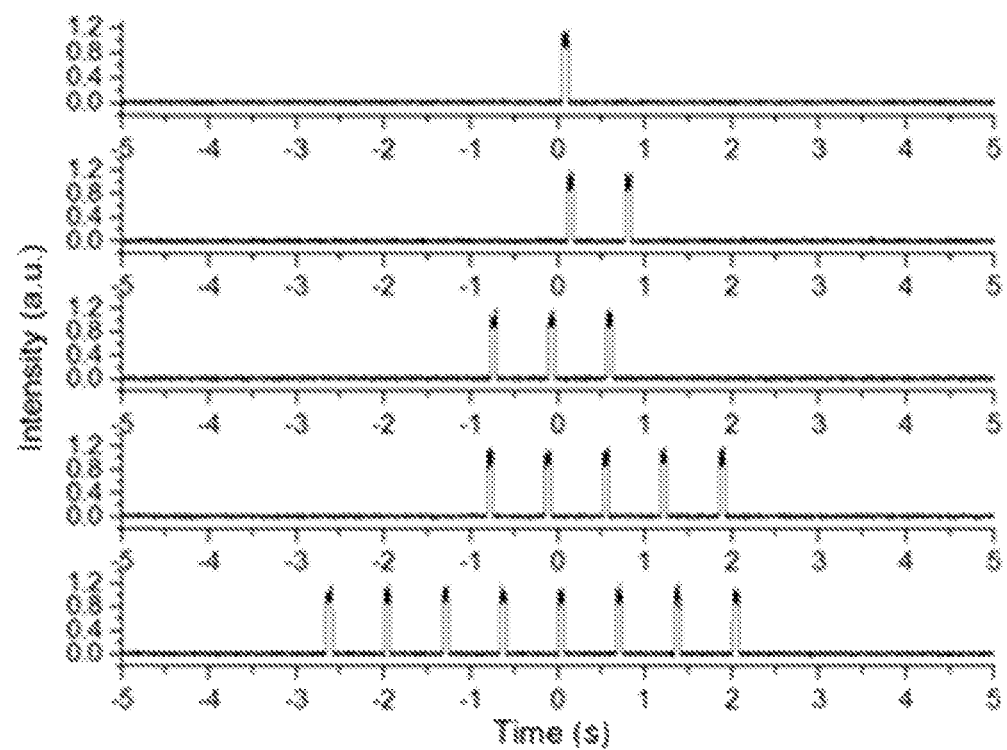

The power, spectral, and temporal characteristics of the prototype 1460-nm laser system were measured. The relationship between output power and driving current is shown in FIG. 16A, where a linear relationship was found. The lasing threshold current was 6.8 A. The power was measured by a thermal power sensor (S310C, Thorlabs, Newton, N.J., USA). FIG. 16B shows the laser spectrum with the output power of 1.2 W, 4.1 W and 6.8 W, respectively. The results were measured by an optical spectrum analyzer (AQ6370C, YOKOGAWA, Tokyo, Japan). The wavelength at the peak power is about 1456 nm. No obvious spectral shift was observed as the output power was increased. The spectral bandwidth increased from 3.1 nm at 1.2 W to 3.9 nm at 6.8 W. Compared with the bandwidth of the water absorption peak (about 100 nm), the influence of this spectral broadening on the LTC may be neglected. The temporal features of this laser system were measured by a photodetector (PDA10CF, Thorlabs, Newton, N.J., USA) and an oscilloscope (MSO4104B-L, Tektronix, Beaverton, Oreg., USA). FIG. 16C demonstrates the temporal shapes of output pulses with pulse widths of 100 ms, 200 ms, and 300 ms. FIG. 16D shows the output pulse trains with the pulse numbers following the Fibonacci sequence, demonstrating that the output pulse number can be precisely controlled by the working duration.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

We claim:

1. A method of laser thermal conjunctivoplasty, comprising:
    delivering laser light from a handheld laser probe to a conjunctival fold; the handheld laser probe comprising:
    a pair of forceps having grasping regions; and
    a line focused laser coupled to the pair of forceps, wherein the forceps are configured to grasp the conjunctival fold and hold the conjunctival fold in a focal plane of a light beam of the line focused laser, and wherein the light beam is focused into a line parallel to and just above the grasping regions of the forceps, and has a wavelength, power, and pulse duration which are configured to uniformly heat the conjunctival fold held in the forceps to a temperature high enough for shrinking a thickness of the conjunctival fold, thereby performing laser thermal conjunctivoplasty.

2. The method of claim 1, further comprising:
grasping the conjunctival fold with the forceps; and
lifting the conjunctival fold off the sclera and thereby minimizing the chance of damaging the underlying sclera, ciliary body, choroid, and retina.

3. The method of claim 1, wherein the line focused laser is a pulse laser.

4. The method of claim 1, wherein the light beam is focused into a line with a length of about 5 mm to about 15 mm and a width of about 0.5 mm to about 2 mm.

5. The method of claim 1, wherein the line focused laser has a central wavelength with a water absorption length of 1~100 mm$^{-1}$.

6. The method of claim 1, wherein the pulse duration is 5 milliseconds to 500 milliseconds.

7. The method of claim 1, wherein the light beam is focused into a line with a length of about 10 mm.

8. The method of claim 1, wherein the light beam is focused into a line with a width of about 1 mm.

9. The method of claim 1, wherein the light beam is focused into a line with a cylindrical lens.

10. The method of claim 1, wherein the grasping regions of the forceps comprise angled grasping platforms.

11. The method of claim 10, wherein the angled grasping platforms are angled about 30° to about 90° relative to a long axis of the forceps.

12. The method of claim 1, wherein the light beam is configured to uniformly heat the conjunctival fold held in the forceps to a temperature between 55° C. and 80° C.

13. The method of claim 3, wherein the wavelength is about 1.3 µm to about 2.4 µm.

14. The method of claim 13, wherein the wavelength has a water absorption coefficient of 0.1 cm$^{-1}$ to 100 cm$^{-1}$.

15. The method of claim 1, wherein the power is between 0.1 and 6.0 W.

* * * * *